US006074630A

United States Patent [19]
Devillez et al.

[11] Patent Number: 6,074,630
[45] Date of Patent: Jun. 13, 2000

[54] DELIVERY SYSTEM FOR SUNCARE PRODUCTS

[76] Inventors: Richard L. Devillez, DCDT, 2220 CR 467, Hondo, Tex. 78861; James McShane, 3110 Raleigh Ridge Cove, Memphis, Tenn. 38128

[21] Appl. No.: 09/447,802

[22] Filed: Nov. 23, 1999

[51] Int. Cl.[7] ............................... A61K 7/42; A61K 7/44; A61K 7/00; D03D 25/00
[52] U.S. Cl. .............................. 424/59; 424/60; 424/400; 424/401; 428/245; 428/260
[58] Field of Search ................................ 424/89, 60, 400, 424/401

[56] References Cited

U.S. PATENT DOCUMENTS

| | | | |
|---|---|---|---|
| 4,563,346 | 1/1986 | Deckner | 424/59 |
| 5,047,232 | 9/1991 | Kaplan | 424/59 |
| 5,093,107 | 3/1992 | Matravers | 424/59 |
| 5,178,852 | 1/1993 | Forestier et al. | 424/60 |
| 5,229,104 | 7/1993 | Sottery et al. | 424/59 |
| 5,232,688 | 8/1993 | Ziegler et al. | 424/59 |
| 5,318,774 | 6/1994 | Alban et al. | 424/59 |
| 5,445,815 | 8/1995 | Siegfried | 424/59 |

*Primary Examiner*—Shelley A. Dodson
*Attorney, Agent, or Firm*—Richard C. Litman

[57] ABSTRACT

A delivery system for sunscreen products that applies a dry, waterproof sunscreen composition to the skin. The delivery system for suncare products of the present invention is designed to apply only the required amount of sunscreen composition to the skin without excess. The sunscreen composition is applied to an article such as paper, nonwoven cloth or porous plastic which is subsequently rubbed onto the skin. Alternatively, the sunscreen may take the form of a wafer or a bar with or without a support article. A delivery system for suncare products which include dihydroxyacetone in order to produce a semi-permanent color that gives the appearance of a natural suntan is described which utilizes the same self-leveling principle as the delivery system for suncare products containing sunscreen compositions.

25 Claims, No Drawings

DELIVERY SYSTEM FOR SUNCARE PRODUCTS

BACKGROUND OF THE INVENTION

1. Field of the Invention

The present invention relates to a dry, waterproof sunscreen composition, a method of applying the sunscreen composition (a delivery system for sunscreen products), a sunless tanning dihydroxyacetone based preparation, and a method for applying the dihydroxyacetone based preparation.

2. Description of the Related Art

The undesirable effects of overexposure to sunlight are well known. Such exposure can result in not only an uncomfortable sunburn but in prematurely aging skin, wrinkles, loss of skin elasticity, dermatosis and ultimately skin cancer. Sun screening is desirable in order to protect the skin from these, and other, adverse effects of solar radiation. The most dangerous solar radiation is the ultra violet (UV) radiation at wavelengths lower than 400 nm which includes both UVA and UVB radiation.

The sun protection factor (SPF) is a measure of the protection from the sun afforded by a sunscreen agent or composition containing a sunscreen agent. Compositions having higher SPF values provide more protection from solar radiation and are preferred. As used herein in reference to the compositions of the present invention, the term "Sun Protection Factor" or "SPF" is described in the Federal Register 58(90), entitled "Sunscreen Drug Products for Over-The-Counter Human Use" (1993 Sunscreen Monograph) (the monograph).

Conventional sunscreen compositions are typically in the form of a liquid, either a lotion or a cream. These compositions may be either oil or water based. The water-based emulsion serves mainly as an aid to disperse the active ingredients topically. The carrier water evaporates and leaves a thin film of active ingredients plus excipient deposited on the skin. The film remaining on the skin contains the product which protects the skin from ultraviolet radiation. The liquid applications of these sunscreen compositions are often messy or greasy to the touch. Also, the distribution of the active ingredients on the skin is uneven when using sunscreen compositions containing liquid. The user must wait for the liquid in the sunscreen compositions to dry.

Another limitation of the prior art is that many sunscreen compositions are not waterproof. When sunscreen compositions are waterproof, the user must wait for a specified time for the sunscreen composition to dry and for the waterproofing to become effective. The waterproofing in these compositions can be easily washed off prior to drying. The waterproofing in the current invention is effective instantly upon applying to the skin.

Current sunscreen compositions use emulsifiers to create an emulsion and allow the product to penetrate the skin. They also utilize preservatives which may sensitize the skin. These conventional sunscreen compositions may also irritate the skin. The current invention does not use an emulsion, and does not penetrate the skin, both of which reduces the risk of irritation or an allergic reaction to the skin and systemic immune suppression from repeated use.

Dihydroxyacetone is commonly used in compositions having dihydroxyacetone concentrations ranging from 3 to 8% w/w in the form of a gel, cream, lotion, or spray products. Typically, these products are applied by hand. Sprays are used by spraying the composition on the skin and rubbing the composition on the skin by hand to make the application more uniform.

Many complaints with these products relate to uneven color formation resulting in streaks or blotchiness. Products containing dihydroxyacetone can be applied to the skin to a maximum of about 2–2.5 $mg/cm^2$. Applications exceeding this level cannot be "rubbed in" which leaves the feeling that an excessive amount has been applied. An application of about 2 $mg/cm^2$ is preferable.

Currently available products require the user to estimate the amount of product dispensed and the size of the area that is to be covered. Repeated application at a specific application density is not possible. At application densities of 2 $mg/cm^2$ or below streaking and blotchiness are not as severe but a uniform coating cannot be achieved by hand application. At lower levels (about 1 $mg/cm^2$) the product cannot be uniformly spread over the skin because of the affinity of the skin for the small amount of dihydroxyacetone preparation present. The result is streaking and blotchiness. The resultant color variation is caused by the presence of some skin areas having virtually no coverage by the product.

U.S. Pat. No. 4,563,346 issued to Deckner on Jan. 7, 1986 discloses a delivery system for delivering topically active ingredients to the skin wherein the delivery system is formed of a water-in-volatile silicone emulsion which includes an interior water phase and an exterior silicone phase which contains the active ingredient to be topically applied. The preferred delivery system of Deckner includes a volatile silicone (decamethyl cyclopentasiloxane), a non-ionic emulsifier (dioleyl methyl glucaside), deionized water and alcohol. The sunscreen emulsion formulation of Deckner contains octyldimethyl p-aminobenzoic acid in addition to the ingredients of the delivery system. Once the sunscreen emulsion formulation of Deckner is applied to the skin, the water and volatile silicone evaporate, leaving a film of sunscreen agent on the skin which is resistant to water and perspiration, but is removable by washing with soap.

U.S. Pat. No. 5,047,232 issued to Kaplan on Sep. 10, 1991 shows a non-aqueous waterproof oil-based topical composition containing one or more water-in-oil emulsifiers and at least one cosmetic emollient. Also, in Kaplan there is disclosed a method for preparing a non-aqueous waterproof oil-based topical sunscreen composition. The sunscreen composition of Kaplan is an oil based liquid composition which is oily to the touch and has the other qualities of oil as well. U.S. Pat. No. 5,093,107 issued to Matravers on Mar. 3, 1992 describes a skin protective sunscreen composition, and method of making same, exhibiting enhanced water repellency and conditioning effects comprising ultraviolet blockers, aliphatic waxes and hydrophobic silicones disposed in a pharmacologically acceptable water-free carrier. The sunscreen composition of Matravers is water repellent, moisturizes the skin, and has a pleasant feel. The base contains a synthetic aliphatic wax which is a high molecular weight $C_{16}$–$C_{36}$ saturated synthetic wax fatty acid admixed with one or more hydrophobic silicones into which one or more sunscreens is uniformly dispersed. The hydrophobic silicones include cyclomethicone, dimethiconol, dimethicone, phenyltrimethicone and the like. The sunscreen base can be utilized with a variety of conventional sun blockers.

U.S. Pat. No. 5,178,852 issued to Forestier et al. on Jan. 12, 1993 discloses cosmetic and pharmaceutical compositions containing derivatives of benzylidenecamphor which are wide-band sunscreens and antioxidants and are utilized in the treatment of cutaneous inflammations and allergies. Although the benzylidenecamphor compounds could be utilized in a variety of compositions, the compositions shown in Forestier et al. include water, oils and/or waxes.

U.S. Pat. No. 5,620,682 issued to Fogel on Apr. 15, 1997 discloses a variety of sunscreen compositions containing an emollient which is a neopentanoate ester. The neopentanoate ester of the Fogel Patent is an excellent skin moisturizer and serves the additional function of increasing the SPF factors of the sunscreen compositions. All of the sunscreen compositions prepared according to Fogel are liquids, and no solid/dry form of sunscreen composition is contemplated by Fogel.

U.S. Pat. No. 5,447,715 issued to Roberts on Sep. 5, 1995 describes a non-aqueous sunscreen composition containing an amount of a volatile silicone oil sufficient to maintain the SPF of the waterproof composition at a value greater than about 20, and a conventional non-aqueous sunscreen formulation or a conventional non-aqueous waterproof sunscreen formulation. The composition of Roberts could be a liquid, a gel or a semi-solid. This composition contains many ingredients including ozokerite wax, lauryl lactate, microcrystalline wax, carnauba wax, polybutene, otyl methoxycinnamate, octyl dimethyl PABA, benzophenone-3, benzoic acid, propyl paraben, octadecene-1/maleic anhydride, copolymer, talc, fragrance and Dow Corning 344 fluid. The Roberts patent does not disclose a solid sunscreen composition. Also, the more ingredients found in a topical composition, the greater the chance of an allergic response.

U.S. Pat. No. 5,445,815 issued to Siegfried on Aug. 29, 1995 shows a dry sunscreen composition which includes a highly cross-linked polymethacrylate copolymer powder combined with active sunscreen ingredients. The composition includes octyl methoxycinnamate, octyl salicylate, homosalate, menthyl anthranilate, actocrylene, benzophenone-3, propylparaben, BHT, PVP/eicosene copolymer, $C_{12-15}$ alcohols benzoate, octyldodecyl neopentanoate, titanium dioxide, D&C yellow No. 5 aluminum lake and acrylates copolymer. The dry sunscreen of Siegfried utilizes a highly cross linked polymethacrylate copolymer powder as the application vehicle.

U.S. Pat. No. 5,676,934 issued to Siegfried on Oct. 14, 1997 discloses a dry sunscreen composition comprising effective amounts of octyl methoxycinnamate, octyl salicylate, homosalate, menthyl anthranilate, octocrylene, benzophenone-3, propylparaben, BHT, PVP/eicosene copolymer, octyldodecyl neopentanoate, $C_{12-15}$ alcohol, benzoate, titanium dioxide and acrylates copolymer, and a method for making the dry sunscreen. A homogeneous dry sunscreen is disclosed by Siegfried. The sunscreen composition therein utilizes entrapment polymers, such as acrylates copolymers. The resultant dry sunscreen composition is a homogenous powder.

U.S. Pat. No. 5,747,010 issued to Geesin et al. on May 5, 1998 describes a method for protecting skin from the oxidative effects of ultraviolet A radiation including UVA-induced lipid peroxidation. The method disclosed therein comprises topically applying to the skin an effective amount of a photoprotective composition that contains a lipophilic antioxidant that does not have appreciable absorbance near wavelengths of 320–380 nm. The photoprotective compositions of Geesin can be in solid, liquid or aerosol form. The compositions can be formulated into a liposomal formulation, an emollient, a liquid, a cream, a gel, an ointment, a microemulsion, or a solution. The lipophilic antioxidant disclosed in Geesin includes butylated hydroxyanisole, butylated hydroxytoluene and ascorbyl-6-palmitate. Also, the sunscreen composition may include a sunblock agent and/or a sunscreen agent. The sunblock may include zinc oxide or titanium dioxide, and the sunscreen agent may include p-aminobenzoic acid and its derivatives, anthranilates, salicylates, cinnamates and their derivatives, naphtholsulfonates, benzophenones, dibenzoylmethane derivatives, and tannic acid and its derivatives. The protective means of Geesin is not, per se, a sunscreen composition but is a method of protecting the skin from the oxidative effects of ultraviolet radiation and is a fundamentally distinct invention from the present invention. Also, Geesin's means does not include waterproofing.

U.S. Pat. No. 5,700,452 issued to Deckner et al. on Dec. 23, 1997 describes emulsion compositions which are useful for imparting both an artificial tan to human skin and for providing protection to the skin from the harmful effects of UV radiation. The invention of Deckner et al. utilizes dihydroxyacetone in an oil-in-water emulsion sunscreen composition. The emulsion compositions do not address the need addressed by the current invention because, although both sunscreen and an artificial tan are addressed, there is no provision for the even application of the composition.

U.S. Pat. No. 5,705,145 issued to Miklean et al. on Jan. 6, 1998 discloses cosmetic compositions for providing an artificial tan to skin which comprises dihydroxyacetone and an azole in an acceptable carrier and a method for using the same. The invention of Miklean et al. does not provide a combination artificial tan and sunscreen. Also, a dry, even application is not provided for in Miklean et al., as an oil-in-water emulsion is utilized.

U.S. Pat. No. 5,741,480 issued to Ascione on Apr. 21, 1998 shows an artificial tanning cosmetic composition containing dihydroxyacetone, among other components. The cosmetic composition of Ascione is a water-in-silicone emulsion and does not include a sunscreen composition. It is unlike the present invention in that it does not contain a waterproof dry sunscreen composition as well as the dihydroxyacetone, nor does it provide for an even distribution of the composition claimed therein.

U.S. Pat. No. 5,229,104 issued to Sottery et al. on Jul. 20 1993 describes oil-in-water emulsion compositions useful for imparting an artificial tan to human skin. The emulsions therein contain paucilamellar lipid vesicles encapsulating an aqueous dihydroxyacetone solution. The invention of Sottery et al. may include sunscreen compositions. The oil-in-water emulsion composition does not contain waterproofing components and does not eliminate the potential for uneven distribution of the suncare composition.

U.S. Pat. No. 5,232,688 issued to Ziegler et al. on Aug. 3, 1993 discloses a composition and method for self-tanning of the skin which may include dihydroxyacetone and a variety of potential carriers. The invention of Ziegler et al. does not, however, include a sunscreening component. The Ziegler composition therefore does not meet all of the potential uses of the present invention in that it does not provide for even distribution of sunscreen and artificial tanning compositions on the skin.

U.S. Pat. No. 5,318,774 issued to Alban et al. on Jun. 7, 1994 describes stabilized compositions, preferably in the form of oil-in-water emulsions, for imparting an artificial tan to human skin. The water phase of these compositions contains dihydroxyacetone, as well as other compounds, and the oil phase contains fatty acids or derivatives thereto. These compositions may, alternatively, include one or more sunscreen agents. The invention of Alban et al. does not address the need for dry, waterproof suncare products. It also does not address the need for even distribution of the suncare compositions.

U.S. Pat. No. 5,514,367 issued to Lentini et al. on May 7, 1996 shows cosmetic compositions for artificially tanning the skin utilizing skin tanning agents and cyclodextrins. Dihydroxyacetone is an acceptable skin tanning agent to be utilized in the invention of Lentini et al. The cosmetic compositions therein are applied by hand or in a manner otherwise analogous to a method for applying cosmetics. The invention of Lentini et al. does not address the potential for uneven application of suncare products nor does it address the aspects of waterproofing and sunscreening.

U.S. Pat. No. 5,603,923 issued to Robinson et al. describes artificial tanning compositions which provide improved color development, and good chemical and physical stability. These artificial tanning compositions include dihydroxyacetone. The compositions of Robinson et al. tend to utilize oil-in-water emulsions or other emulsifiers and do not have the capacity for even application of the present invention.

U.S. Pat. No. 5,656,262 issued to Kurz et al. discloses skin-coloring powder mixtures which may contain dihydroxyacetone. Sunscreen agents may also be utilized in conjunction with the skin-coloring powder mixtures. The powder mixtures of Kurz et al. are designed to be utilized in cosmetic or pharmaceutical preparations which vary from gels to solid sticks but they are not designed to be evenly applied in the same manner as the present invention.

There is a strongly felt need for a dry sunscreen composition which eliminates the difficulties of the prior art. The term "dry" herein refers to non-emulsion, non-aqueous and oil-free; the term does not refer to a solid nor does it preclude a low viscosity liquid. A dry sunscreen composition, which is non-emulsion, non-aqueous, and that does not include oils, is desirable because such a composition would be less messy and would tend to distribute the active ingredient more evenly. Also, a waterproof sunscreen composition having a high SPF value is very desirable. It is especially advantageous to have a waterproof sunscreen composition that is applied dry so that no time must elapse prior to the sunscreen composition becoming waterproof.

In addition, there is a strong felt need for an ever application of dihydroxyacetone. A self-leveling application of dihydroxyacetone is ideal. It is desirable to have a dihydroxyacetone application which can be applied from a cloth or other application matrix and not require sprays, lotions or creams.

None of the above inventions and patents, taken either singularly or in combination, is seen to describe the instant invention as claimed. Thus, a delivery system for suncare products solving the aforementioned problems is desired.

SUMMARY OF THE INVENTION

Accordingly, it is a principal object of the invention to provide a safe and effective dry sunscreen composition and a delivery system for the sunscreen composition. The sunscreen composition contains at least a waterproofing agent and a sunscreen agent. The sunscreen composition utilized in this invention is not messy and since it is applied in a dry state it covers the desired area of the skin evenly without any areas containing an excessive amount of the active ingredients in the sunscreen composition. The application substrate controls the amount of sunscreen per square centimeter that can be delivered onto the skin. Additional applications will not apply heavier levels of sunscreen to the skin because the amount of the product applied to the skin is controlled by the relative affinity of the product to the skin and to its applicator; this phenomenon is referred to hereinafter as self-leveling.

Self-leveling is also apparent in the application of dihydroxyacetone. The dihydroxyacetone sunless tanning composition is in an aqueous solution and may contain a sufficient amount of emulsifier to produce an effective emulsion. The resultant dihydroxyacetone sunless tanning composition is self-leveling. The composition is disposed on a porous or fibrous substrate serving as an applicator which is applied to the skin by wiping the applicator on the skin. The amount of the product applied to the skin is controlled by the opposing capillary attractive forces of the dihydroxyacetone composition for the applicator and its affinity for the skin.

It is another object of the invention to provide a sunscreen composition, and a delivery system for the sunscreen composition, which has greater SPF values with the same application density. The sunscreen composition of the present invention has a means for application, the delivery system for suncare products, wherein the applicator is labeled to treat a certain amount of skin so that sufficient sunscreen will be available to adequately and completely coat the skin with a controlled concentration of sunscreen. The method of application controls the amount of active sunscreen agents that is applied per square centimeter.

It is a further object of the invention to have a sunscreen delivery system which applies a sunscreen composition that has superior waterproofing properties which is also effective upon application.

It is an object of the invention to provide a system that applies dihydroxyacetone evenly without blotchiness or streaking in the color that develops.

Still another object of the invention is to minimize adverse and allergic reactions due to the addition of unnecessary emulsifiers and other excessive ingredients found in many sunscreen compositions.

It is an object of the invention to provide improved elements and arrangements thereof for the purposes described which is inexpensive, dependable and fully effective in accomplishing its intended purposes.

These and other objects of the present invention will become readily apparent upon further review of the following specification.

DETAILED DESCRIPTION OF THE PREFERRED EMBODIMENTS

The present invention relates to a delivery system for suncare products which applies a dry sunscreen composition directly to the skin. The sunscreen composition has at least a waterproofing agent and a sunscreen agent. Additional agents may be added to the composition such as solvents, additional UV affecting compounds etc. Also, more than one waterproofing agent or sunscreen agent may be added as well. The delivery system for sunscreen products can be made with a variety of materials which are suitable as matrices for the type of dry sunscreen compositions disclosed herein. Suitable materials for sunscreen formulas include nonwoven fabrics, paper, or a core of nonporous material, such as polyethylene wafer.

Likewise, a delivery system for aqueous dihydroxyacetone composition is disclosed. The delivery system for dihydroxyacetone is self-leveling and can be applied to the skin using a suitable material. Porous or fibrous materials are required for the delivery system for aqueous dihydroxyacetone compositions.

Nonwoven fabrics are available in different porosities and thicknesses. When the sunscreen composition is in the form of a viscous, nonaqueous liquid, the sunscreen may be applied by using a matrix consisting of a fibrous or porous substrate. The sunscreen application rate to the fabric is determined by capillary attraction. The application and density of the sunscreen formula on the skin is determined by the relative affinity of sunscreen formula for the sunscreen containing fabric and for the skin. The sunbather rubs the fabric on the skin and the appropriate amount of the sunscreen composition will be applied to the skin. Excess rubbing of the fabric on the skin will not add excess sunscreen composition to the skin because of the relative affinity of the sunscreen.

As stated above, a core of nonporous material such as polyethylene which could be coated with a solid layer of the sunscreen composition. A thin saucer shaped wafer 2 to 3 inches in diameter could be coated with a sunscreen composition that has been melted. Preferably the wafer is polyethylene coated with the solidified formula. The wafer is then rubbed on the skin to apply the sunscreen composition to the skin. Alternatively, the wafer could be rubbed on the hands and then the hands could be rubbed on the skin. Additional matrices could be paper or tissues which could be utilized in a similar fashion as previously discussed.

Alternatively, the sunscreen may be applied without a matrix. For example, a dispenser might be utilized to apply the sunscreen composition to the skin in the form of a stick applicator. These applicators would be analogous to antiperspirant stick or gel dispensers. Another suitable means of applying the suncare product would be in a molded form such as a bar (like soap) which could be rubbed on the skin. This molded form is used herein to refer to a metered ointment, or a gel, which are likewise considered types of matrices. When the sunscreen is delivered directly without a matrix, the application rate is solely a function of the composition and hardness of the suncare product. In the present invention, this composition is adjusted so that it contains no emulsifying agents and a minimum of water, so that the sunscreen agent is in higher concentration than with previous suncare formulations, and hence is in solid or dry form.

The proper matrix for the dihydroxyacetone composition includes porous or fibrous substrates. Cotton, polyester, nylon or rayon fiber cloth and nonwoven fabrics such as Thermalbond nonwovens including these fibers as well as fibrous polypropylene, wet process polyester/cellulose fabric combinations, and caustic entangled cotton fabric (manufacture by Veratec Nonwovens). Fibrous bonded nylon pads may also be used.

Manufacturing of the delivery system for suncare products could be accomplished by silk screening or spraying the melted formula onto the nonwoven fabric, tissue, paper, or other porous medium at a controlled uniform rate. The wafer would be coated with enrobing, dipping into the melted sunscreen composition. The sunscreen composition could be melted and then poured into a mold.

Any water insoluble sunscreen solvent which is physiologically suitable for application to the skin may be used. Some waterproofing agents that can be used in the current invention are caprylic/capric triglyceride, lignoceryl erucate, PPG-2-myristyl ether propionate, Di-PPG-3 myristyl ether adipate, diisopropyl adipate and dioctyl maleate. Tricontanyl PVP is preferably used as a waterproofing agent. Other waterproofing agents are PVP/eiconsene copolymer, PVP/hexadecene copolymer, dimethicone and trimethyl siloxy silicate, diiostearyl trimethylol propane siloxy silicate, acetylated lanolin alcohols, acetylated lanolin, cetearyl octanoate, phosphated mono and diglycerides, and behenic acid ester dimethicone. Many other waterproofing agents and suitable solvents are well known and available.

It is desirable to limit the amount of sunscreen agent applied to the skin. The maximum allowable concentration is dictated by the Food and Drug Administration (FDA). The FDA maintains a list of approved sunscreen agents, see table 1, which specifies the concentration of these agents that can be used in suncare products (% allowable sunscreen agent). For example, octylmethoxycinnamate, which is one of the most widely used sunscreen agents, is limited to 7.5% in suncare products. This includes products in liquid and semi-liquid states.

TABLE 1

Approved Sunscreens and Concentrations

| Sunscreen Agent | Concentration (%) |
| --- | --- |
| Aminobenzoic acid (ABA) | 5–15 |
| Glyceryl aminobenzoate | 2–3 |
| Padimate O | 1.4–8 |
| Ethyl 4-[bis(hydroxypropyl)] aminobenzoate | 1–5 |
| Menthyl anthranilate | 3.5–5 |

TABLE 1-continued

Approved Sunscreens and Concentrations

| Sunscreen Agent | Concentration (%) |
| --- | --- |
| Dioxybenzone | 3 |
| Oxybenzone | 2–6 |
| Sulisobenzone | 5–10 |
| Cinoxate | 1–3 |
| Diethanolamine methoxycinnamate | 8–10 |
| Octyl methoxycinnamate | 2–7.5 |
| Octocrylene | 7–10 |
| Avobenzone | 3 (alone); 2–3 (combined) |
| Octyl salicylate | 3–5 |
| Homosalate | 4–15 |
| Trolamine salicylate | 5–12 |
| Digalloyl trioleate | 2–5 |
| Lawsone (L) with dihydroxyacetone (DHA) | 0.25 (L); 3 (DHA) |
| Phenylbenzimidazole sulfonic acid | 1–4 |
| Red petrolatum | 30–100 |
| Titanium dioxide | 2–25 |

Also, all sunscreen formulations when tested for SPF are irradiated on the skin at a concentration of 2 mg/cm$^2$. It is essential therefore to have the delivery system for suncare products deliver the sunscreen agent at an equivalent application rate to that found in lotions. In other words, it is desirable to have the sunscreen agent to be applied to the skin at an equivalent rate to the amount indicated in the FDA rules. The following formula determines the amount of sunscreen per unit area equivalent to a set percentage of sunscreen agent tested for SPF at 2 mg/cm$^2$ and results in the application rate:

Application rate=(2 mg/cm$^2$)(maximum % sunscreen ingredient allowed by FDA)/(% sunscreen agent in sunscreen composition).

Each sunscreen in the composition must be included at a level that is in compliance with the monograph. The content of the compositions for use in this delivery system could include any combination of approved sunscreen agents in any amount. The limiting factor for each ingredient is calculated by selecting the sunscreen that is in the formula at the highest ratio between % sunscreen/ % allowable sunscreen. The application rate for SPF testing for the composition would be calculated based on this sunscreen. The density in mg/cm$^2$ at this application rate would be calculated to insure that each individual sunscreen is in the range of concentration specified in the monograph, i.e., (application rate for SPF testing) (% in composition)/100, must fall in the range of the monograph. See the following examples of the preferred embodiments, for demonstrations on how to use this formula.

By using the equivalent application rate the concentration of sunscreen agent on the skin would be within the range specified by the FDA. As an example, octylmethoxycinnamate is allowed in suncare products at a maximum concentration of 7.5%. At the specified application rate of 2 mg/cm$^2$ the amount of octylmethoxycinnamate per cm$^2$ would be 0.15 mg. At 56% octylmethoxycinnamate when applied for SPF testing at 0.267 mg/cm$^2$ would also have a concentration of 0.15 mg/cm$^2$. The following table lists some maximum and minimum ranges of a few sunscreen compounds.

TABLE 2

Examples of Maximum/Minimum Ranges of Approved Sunscreen Compounds

| Sunscreen | Approved Concentration (%) | Maximum (mg/cm$^2$) | Minimum (mg/cm$^2$) |
| --- | --- | --- | --- |
| aminobenzoic acid (ABA) | 5.0-15 | 0.30 | 0.10 |
| menthylanthranilate | 3.4-15 | 0.10 | 0.07 |
| oxybenzone | 2-6 | 0.12 | 0.04 |
| diethanolamine methoxycinnamate | 8-10 | 0.20 | 0.16 |
| octylmethoxycinnamate | 2-7.5 | 0.15 | 0.04 |
| homosalicylate | 4-15 | 0.30 | 0.08 |
| avobenzone | 2-3 | 0.06 | 0.04 |
| titanium dioxide | 2-25 | 0.50 | 0.04 |

The equivalent application rate is found by application of the above formula for a given concentration of sunscreen agent. A matrix is then selected, by a process of trial and error, which limits the application rate to the equivalent application rate. The matrix is selected for its density and porosity, so that the application rate is appropriately limited. Limitation of the application rate is governed by the differing affinity of the sunscreen agent for the skin and for the matrix. Preferably, the matrix provides a dense, uniform application of the sunscreen product to the skin at the first stroke over the skin. Hence, subsequent rubbing of the matrix over a previously coated area of the skin does not result in the deposition of additional suncare product, due to the limited affinity of the skin for the suncare product relative to the affinity of the matrix for the suncare product.

The delivery system for sunscreen products is self leveling. The force of adhesion is stronger than the force of cohesion. A monolayer of the sunscreen composition is transferred to the skin by direct contact with the solid product, or by application of a viscous, nonaqueous liquid on a fibrous or porous substrate. Skin so coated does not have the ability to attract additional sunscreen composition, thus limiting the amount of sunscreen agent that can be applied per unit area. Rubbing additional sunscreen composition (in a matrix) on previously treated skin would not change the thickness of the sunscreen agent on the skin significantly.

The skin-coloring agent most frequently and effectively used is dihydroxyacetone. A uniform color is produced without streaks or blotchiness. Almost instant drying is a desirable aspect of the current invention. The product can be reapplied with the same application density. The absorbent substrates mentioned previously are aesthetically suitable and nonreactive towards dihydroxyacetone. The treated cloth or pad is rubbed over the skin area to be colored. Within about 2-4 hours a brown color develops (as with any dihydroxyacetone product). The substrate can be cloth or pad. It can be composed of laminated materials, for example, a cloth with a less dense inner layer and with an outer layer or layers made of material having higher capillary attraction for liquids. The dihydroxyacetone on the cloth or pad is bound by capillary attraction and is not free to saturate or overwet the skin.

Untreated skin when in contact with the pad or cloth has sufficient attraction to be wetted by the solution to a predetermined concentration of less than about 2 mg/cm$^2$. No amount of additional rubbing of the treated area will result in significantly higher amounts of dihydroxyacetone composition being deposited on the skin. Any untreated area will be wetted with the aqueous dihydroxyacetone solution to the same concentration as the treated areas.

The color intensity produced by dihydroxyacetone on the skin is dependent on two factors: the amount and/or type of amine reactor sites per unit area available to react with the dihydroxyacetone, and the amount of dihydroxyacetone per unit area applied. Typically, the formulation of the cream, spray, solution, powder or other composition appears to have no effect on the color intensity produced. Commonly darker formulations will contain 7% dihydroxyacetone. Using 2 mg/cm$^2$ as a standard application rate, the amount of dihydroxyacetone applied to the skin would be (2 mg.cm$^2$) (0.07)=0.14 mg DHA/cm$^2$. Most skin types are able to react with more than 0.14 mg DHA/cm$^2$.

In contrast, by using a cloth or pad matrix the amount of color that develops on the skin is controlled by two factors: the concentration of dihydroxyacetone in the solution, which is typically 15 to 60% w/w in water, and the relative affinity for the dihydroxyacetone solution between the cloth or pad and untreated skin. The treated skin has less affinity for the composition containing dihydroxyacetone than the cloth, pad or untreated skin, and cannot attract additional dihydroxyacetone solution.

The selection of the porous solid (matrix), the percentage of dihydroxyacetone in the solution, and the ratio between the porous solid dry weight and the weight of the dihydroxyacetone solution added to the porous solid determine the color intensity produced on the skin. A 60% dihydroxyacetone solution that is deposited on the skin at 0.2 mg/cm$^2$ (0.12 mg DHA/cm$^2$) will produce less color than a 30% dihydroxyacetone solution that is deposited on the skin at 0.5 mg/cm$^2$ (0.15 mg DHA/cm$^2$)

Generally, any substrate (matrix) that is composed of pores of fibers when wetted with a liquid holds the liquid by capillary attraction. When such a substrate is in contact with another surface, the liquid will equilibrate between the two surfaces. As the weight increases and with a given amount of dihydroxyacetone solution, the change in the ratio between the substrate and the solution is smaller as solution is removed from the substrate. As the fibers are smaller in diameter and are more compacted, the affinity or capillary attraction towards absorbed liquids is increased.

A profile is a procedure that evaluates specific systems, in this case, substrates and dihydroxyacetone formulations. The following profile for 30% dihydroxyacetone in water on Sontara® nonwoven polyester 4"×4" is presented in the following table 3.

TABLE 3

Profile for 30% Dihydroxyacetone solution in water

| DHA solution remaining on pad in grams | mg of DHA solution applied | mg/cm$^2$ applied | ratio: solution/dry cloth |
|---|---|---|---|
| 4.919 | 69 | 1.18 | 5.666 |
| 4.772 | 62 | 1.06 | 5.574 |
| 4.700 | 66 | 1.14 | 5.490 |
| cloth blotted with tissue on both sides to remove some dihydroxyacetone solution | | | |
| 3.494 | 61 | 1.05 | 4.08 |
| 3.413 | 78 | 1.34 | 3.99 |
| second blotting of cloth with tissue on both sides | | | |
| 2.430 | 70 | 1.21 | 2.64 |
| 2.383 | 46 | 0.79 | 2.80 |
| 2.318 | 66 | 1.14 | 2.70 |
| third blotting of cloth with tissue on both sides | | | |
| 1.143 | 46 | 0.79 | 1.28 |
| 1.075 | 60 | 1.03 | 1.26 |
| fourth blotting of cloth with tissue on both sides | | | |
| 0.798 | 23 | 0.380 | 0.932 |
| 0.751 | 46 | 0.780 | 0.877 |
| 0.731 | 28 | 0.480 | 0.854 |

The profile, in table 3, shows the self-leveling of the dihydroxyacetone solution from an initial weight of 4.919 until the weight of the solution on the cloth dropped to 1.075. In other words, this system can deliver 3.844 grams of 30% dihydroxyacetone solution in a controlled self-leveling manner.

It delivers an average of 1.07 mg/cm$^2$ which is sufficient to produce a dark tan. The skin area that can be treated with this amount of dihydroxyacetone solution is given by (3.844 g/0.00107 g/cm$^2$)=3,592 cm$^2$. This amount is sufficient to treat either the arms or the legs. A progressively lighter tan would result from reducing the 30% dihydroxyacetone content to about 7%. This would be equivalent to a 2 mg/cm$^2$ of a 3.5% conventional dihydroxyacetone lotion (0.07 mg DHA/cm$^2$). For multiple treatments or full body treatment, the size of the dihydroxyacetone solution containing cloth can be calculated.

As used herein, all percentages (%) are percent weight to weight, also expressed as weight/weight %, %(w/w), w/w, w/w % or simply %, unless otherwise indicated.

In general, the sunscreen product may contain about 0–40% PVP/Hexadecene Copolymer or other waterproofing agent, about 7.5–8.0% Octylmethoxycinnamate or other sunscreen agent, about 10–80% total sunscreens, about 0–60% total waterproofing agent, about 0–40% total solvents, and about 0–30% total viscosity modifiers. The following examples are preferred embodiments of the delivery system for suncare products according to the present invention. It is to be noted, however, that these examples are by no means limitations of the invention and that various modifications, and improvements in the manufacturing process, all fall under the scope of this invention. Polyvinyl pyrilidone is referred to as PVP.

EXAMPLE 1

| | |
|---|---|
| Tricontanyl PVP | 12.00% |
| Octylmethoxycinnamate | 58.56% |
| Benzophenone | 23.44% |
| Octyl palmitate | 6.00% |

The equivalent application rate (eq. ap. rate) for example 1 is $$\text{eq. ap. rate} = (2 \text{ mg/cm}^2)(7.5\%)/58.56\% = 0.256 \text{ mg/cm}^2.$$

A preferred method of making the sunscreen composition of the delivery system for suncare products of Example 1 comprises the following steps. Weigh out each ingredient and add to a suitable container. Heat the resulting liquid with gentle stirring to 60° C., and mix to uniformity.

A preferred method of making the delivery system for suncare products utilizing the composition of Example 1 comprises the following additional steps. Allow the sunscreen composition liquid to cool to 45° C. Add the cooled liquid to a cloth substrate, preferably Sontara® polyester fabric (No. 8003), and allow to equilibrate at 45° C. until the cloth is uniformly coated with the liquid. The cloth containing the sunscreen composition is allowed to cool and solidify. The resulting product is ready for use. It will be understood that the cloth must be tested in conjunction with the particular composition described above in order to assure that the composition is applied at the equivalent application rate of 0.256 mg/cm².

EXAMPLE 2

| | |
|---|---|
| Tricontanyl PVP | 20.00% |
| Octylmethoxycinnamate | 32.46% |
| Isostearyl neopentanoate | 34.56% |
| Avobenzone | 12.96% |

The equivalent application rate for example 2 is $$\text{eq. ap. rate} = (2 \text{ mg/cm}^2)(7.5\%)/32.46\% = 0.462 \text{ mg/cm}^2.$$

A preferred method of making the sunscreen composition of the delivery system for suncare products of Example 2 is the same as that for making the composition of Example 1.

A preferred method of making the delivery system for suncare products utilizing the composition of Example 2 comprises the following additional steps. Allow the sunscreen composition liquid to cool to 45° C. Add the cooled liquid to a cloth substrate and allow to equilibrate at 45° C. until the cloth is uniformly coated with the liquid. The cloth containing the sunscreen composition is allowed to cool and solidify. The resulting product is ready for use. Preferably a nonwoven cloth made of polyester is used. In solid formulas like Examples 1 and 2, the application rate in controlled by the formula composition which determines the application rate on the skin. In general, the hardness of the composition controls the application rate.

EXAMPLE 3

| | |
|---|---|
| Tricontanyl PVP | 6.00% |
| Octylmethoxycinnamate | 38.12% |
| Avobenzone | 10.16% |
| Oxybenzone | 10.16% |
| Homomenthyl Salicylate | 35.56% |

The equivalent application rate for Example 3 is given by:

$$\text{eq. ap. rate} = (2 \text{ mg/cm}^2)(7.5\%)/38.12\% = 0.39 \text{ mg/cm}^2.$$

A preferred method of making the sunscreen composition of the delivery system for suncare products of Example 3 is the same as that for making the composition of Example 1.

A preferred method of making the delivery system for suncare products utilizing the composition of Example 3 comprises the following additional steps. Pour the liquid into a conventional plastic tube containing means to dispense a ribbon of a specified length for treating specific body areas, or package in a bottle fitted with a metering pump. Allow the liquid to cool. The resulting product is ready for use. The application rate, in Example 3, is controlled by the affinity to the fibrous or porous substrate by capillary action. Once dispensed the inherent self leveling will result in a very uniform coverage. Alternatively, the sunscreen composition of Example 3 can be packaged in the same manner as in Examples 1 and 2. The formulation of Example 3 is a liquid and it is preferably delivered on a fibrous or porous substrate. It will be understood that the equivalent application rate is achieved in this Example solely by the properties of the composition with regard to its affinity for the skin and the matrix. Liquid formulas are self-leveling due to the opposing attraction of the skin and the capillary attraction of the porous or fibrous substrate for the formulation.

EXAMPLE 4

| | |
|---|---|
| PVP/Hexadecene copolymer | 3.0% |
| Tricontanyl PVP | 3.0% |
| Micronized zinc oxide | 36.0% |
| Silica dimethyl silycate | 1.0% |
| Homomenthyl salicylate | 30.0% |
| Octylmethoxycinnamate | 27.0% |

A preferred method of making the sunscreen composition of the delivery system for suncare products of Example 4 comprises the following steps. Weigh out each ingredient and add to a suitable container. Heat the ingredients to 60° C., and disperse the zinc oxide with high shear mixing while still liquid. Pour the liquid, before cooling, into a stick package (such as conventionally used with antiperspirant sticks) for preparation of a stick applicator and allow to cool and solidify. The resulting product is used by direct application of the molded stick to the skin without a matrix. It will be understood that the equivalent application rate is achieved in this Example solely by the properties of the composition with regard to its affinity for the skin and its hardness.

Some examples of delivery of a suncare product containing dihydroxyacetone are given below.

EXAMPLE 5

| | |
|---|---|
| Dihydroxyacetone | 6.0% |
| Deionized Water | 94.0% |

The dihydroxyacetone is dissolved in water forming a clear solution. The resultant solution is allowed to absorb into Sontara® nonwoven polyester cloth at a ratio of 1 gram of polyester per 5.66 grams of solution. The treated polyester is used to wipe the skin area to be treated.

EXAMPLE 6

The dihydroxyacetone solution of Example 5 was absorbed into cotton pads (Sentinel Item No. 3780) at a ratio of 1 gram on cotton pad per 6.72 grams of dihydroxyacetone solution.

EXAMPLE 7

| | |
|---|---|
| Pluronic F-127(BASF) (Poloxamer 407 NF) | 1.0% |
| Dihydroxyacetone | 6.0% |
| Ethyl Alcohol SDA-40 (200 Proof) | 30.0% |
| Deionized Water | 63.0% |

The solution was absorbed into a bonded nylon fiber pad (Richmond Filtrona) No. 5 at a ratio of 1 gram of nylon pad per 4.86 grams of the dihydroxyacetone solution.

Alternatively, the solution of Example 7 was absorbed into Sentinel Cotton Pads #3780 at a ratio of 1 gram of cotton pad per 6.7 grams of dihydroxyacetone solution. Pluronic F-127 was added as a spreading, wetting agent.

EXAMPLE 8

| | |
|---|---|
| Pluronic F-127 (BASF) (Poloxamer 407 NF) | 1.0% |
| Dihydroxyacetone | 6.0% |
| Ethyl Alcohol SDA-40 (200 Proof) | 30.0% |
| Caramel Color (Acid Proof) | 1.5% |
| Deionized Water | 61.5% |

Caramel color was added as an indicator to insure that no skin area was missed with the applicator. It was prepared and added to nylon pads as in Example No. 7.

Testing of the sample delivery systems, as applied to the sunscreen compositions, is described as follows. A procedure used to test the SPF of the delivery system for suncare products is as follows. UV radiation was supplied by a single port solar simulator (Solar Light Com) equipped with a 150-watt xenon arc. A spectral output similar to that of the natural solar spectrum is obtained by using a combination of the UG-5 and WG-320 filters, each approximately 1 mm in thickness, (Schott Glass Technologies) placed in the emission path. The output of the solar simulator was monitored with a 3D-600 meter (Solar Light Co.). To determine the subject's natural minimal erythema dose (MED) (i.e., the exposure time needed to cause pink skin), each subject received seven radiation exposures on seven adjacent unprotected skin sites on the lower back. Each exposure represents a 25% increase in energy over the previous exposure. On day 2, approximately 24±2 hours after irradiation on visit 1, the irradiated sites were examined for erythema using a four-point scale. The site receiving the lowest dose of UV which produced erythema extending to the borders was selected as the MED for the subject. To determine the subject's MED with sunscreen, a test area of approximately 50 cm$^2$ (5 cm×10 cm) was treated with sunscreen at an application rate of 0.15 mg/cm$^2$. A 50 cm$^2$ test area required the application of approximately 7.5 mg of test material to the respective test areas. The standard (Homomenthyl Salicylate—SPF 4) was used according to the Tentative Final Monograph and applied at an application rate of 2 mg/cm$^2$. A 50 cm$^2$ test area required the application of approximately 100 mg of standard to the respective test area. Fifteen minutes after application, the subject received seven radiation exposures on seven adjacent unprotected skin sites on the lower back according to the 1993 Sunscreen Monograph. Approximately 24 hours after this irradiation, the irradiated sites were examined for erythema using the four point scale. The site treated with the lowest dose of combined UV producing erythema extending to the borders was selected as the MED for the sunscreen protected subject. The SPF is the ratio of the MED from protected skin divided by the MED from unprotected skin. The mean SPF value for Example 1 was 18.43 and for Example 2 was 17.97.

The method of testing the effectiveness of the matrix in achieving the equivalent application rate is illustrated by application to a cotton pad matrix as follows. Cotton circles were allowed to absorb melted sunscreen composition as herein presented and were placed in an aluminum weighing dish. A strip of aluminum about 2 cm wide was made into a handle and stapled to the cloth circle. The treated cotton pad was weighed and rubbed over the skin area and reweighed giving the amount of sunscreen composition deposited on the skin. The area of the skin upon which the cotton pad was measured. Division of the weight of sunscreen composition deposited by the surface area treated provided a measure of the application rate. A dry control was also used to ensure that the cotton pad did not gain weight as a result of absorbance of oils from the skin. Similar testing methods may be used in testing the effectiveness of other matrix materials.

It is to be understood that the present invention is not limited to the embodiments described above, but encompasses any and all embodiments within the scope of the following claims.

We claim:

1. A method of delivering a sunscreen product, comprising the steps of:
   a) selecting a sunscreen agent;
   b) adding at least a waterproofing agent to said sunscreen agent in order to formulate an anhydrous, nonemulsified sunscreen composition having a high concentration of sunscreen agent;
   c) determining a maximum allowable concentration of said sunscreen agent as a weight to weight percentage;
   d) determining the percentage of said sunscreen agent in said sunscreen composition by percentage weight of sunscreen agent to total weight of the composition;

e) determining an equivalent application rate by multiplying said maximum allowable concentration by 2 mg/cm$^2$ and dividing by the percentage of sunscreen agent in said sunscreen composition;

f) selecting a matrix for delivering said sunscreen composition to the skin of a user at said equivalent application rate; and g) disposing said sunscreen composition in and on said matrix.

2. The method of delivering a sunscreen product according to claim 1, wherein said step of adding at least a waterproofing agent further comprises the step of adding an anhydrous solvent.

3. The method of delivering a sunscreen product according to claim 1, wherein said step of adding at least a waterproofing agent further comprises the step of adding a viscosity modifier.

4. The method of delivering a sunscreen product according to claim 1, wherein said step of selecting a matrix further comprises selecting the matrix from the group consisting of paper, nonwoven cloth fabric, a nonreactive thermoplastic material, and a polyethylene wafer.

5. The method of delivering a sunscreen product according to claim 1, wherein said step of selecting a matrix further comprises selecting the matrix from the group consisting of paper, nonwoven cloth fabric, polyethylene, polypropylene, and a polyethylene wafer.

6. The method of delivering a sunscreen product according to claim 1, wherein said step of selecting a matrix further comprises selecting a porous matrix.

7. The method of delivering a sunscreen product according to claim 1, wherein said step of selecting a matrix further comprises selecting a fibrous matrix.

8. The method of delivering a sunscreen product according to claim 1, wherein said step of selecting a matrix further comprises selecting a matrix from the group consisting of cotton pads, nylon pads, rayon fiber cloth, fibrous polypropylene fabric, wet process polyester-cellulose combination fabrics and caustic entangled cotton fabric.

9. A delivery system for sunscreen products comprising:
a sunscreen composition comprising:
between about 10–80% sunscreen agent;
up to 40% waterproofing agent;
up to 40% solvent;
up to 30% viscosity modifiers; and
a matrix;
wherein, the percentage by weight of said sunscreen agent in said sunscreen composition and the affinity of said sunscreen combination for said matrix relative to the affinity of said sunscreen composition for a user's skin results in application of a maximum allowable concentration of said sunscreen agent to the user's skin;
provided, however, that said sunscreen composition is emulsifier free; and
provided further, that said sunscreen composition is substantially anhydrous.

10. The delivery system for sunscreen products according to claim 9, wherein said matrix is selected from the group consisting of cotton pads, nylon pads, rayon fiber cloth, fibrous polypropylene fabric, wet process polyester-cellulose combination fabrics and caustic entangled cotton fabric.

11. The delivery system for sunscreen products according to claim 9, wherein said sunscreen agent is at least one sunscreen agent selected from the group consisting of octyl methoxycinnamate, homomenthyl salicylate, aminobenzoic acid, glyceryl aminobenzoate, padimate O, ethyl-4[bis (hydroxypropyl)] aminobenzoate, menthyl anthranilate, dioxybenzone, oxybenzone, sulisobenzone, cinoxate, diethanolamine methoxycinnamate, octocrylene, avobenzone, octyl salicylate homosalate trolamine salicylate, digalloyl trioleate laxsone with dihydroxyacetone, phenylbenzimidazole sulfonic acid, red petrolatum, and titanium dioxide.

12. The delivery system for sunscreen products according to claim 9, wherein said waterproofing agent is at least one waterproofing agent selected from the group consisting of Tricontanyl polyvinyl pyrilidone, dimethicone and trimethylsiloxysilicate, diiostearyl trimethylol propane siloxy silicate, acetylated lanolin alcohols, acetylated lanolin, cetearyl octanoate, phosphated mono and diglycerides, and behenic acid ester dimethicone.

13. The delivery system for sunscreen products according to claim 9, wherein said sunscreen composition consists essentially of:
a) about 12.00% Tricontanyl polyvinyl pyrilidone;
b) about 58.56% Octylmethoxycinnamate;
c) about 23.44% Benzophenone; and
d) about 6.00% octyl palmitate.

14. The delivery system for sunscreen products according to claim 9, wherein said sunscreen composition consists essentially of:
a) about 20.00% Tricontanyl polyvinyl pyrilidone;
b) about 32.46% Octylmethoxycinnamate;
c) about 34.56% Crodanol ISNP; and
d) about 12.96% Avobenzone.

15. A delivery system for sunscreen products comprising:
a sunscreen composition comprising:
at least one sunscreen agent;
at least one waterproofing agent; and
wherein, the percentage by weight of said sunscreen agent and the affinity of said composition for the skin of a user permits application of said sunscreen composition in a maximum allowable concentration;
provided, however, that said sunscreen composition contains no emulsifier; and
provided further, that said sunscreen composition is substantially anhydrous.

16. The delivery system for sunscreen products according to claim 15, wherein said sunscreen composition is molded into a bar for application to the skin.

17. The delivery system for sunscreen products according to claim 15, wherein said sunscreen composition is formed into an applicator stick for application to the skin.

18. The delivery system for sunscreen products according to claim 15, wherein said sunscreen composition is formulated as a gel for dispensing from a tube.

19. The delivery system for sunscreen products according to claim 15, wherein said sunscreen composition is formulated as an ointment for dispensing from metered pumps.

20. The delivery system for sunscreen products according to claim 15, wherein said sunscreen composition consists essentially of:

| | |
|---|---|
| Tricontanyl PVP | about 6.00%; |
| Octylmethoxycinnamate | about 38.12%; |
| Avobenzone | about 10.16%; |
| Oxybenzone | about 10.16%; |
| Homomenthyl Salicylate | about 35.56%; | wherein said percentages represent the ratio of the weight of each constituent to total weight of said sunscreen composition.

21. The delivery system for sunscreen products according to claim 15, wherein said sunscreen composition consists essentially of:

| | |
|---|---|
| PVP/Hexadecene copolymer | about 3.0%; |
| Tricontanyl PVP | about 3.0%; |
| Micronized zinc oxide | about 36.0%; |
| Silica dimethyl silycate | about 1.0%; |
| Homomenthyl salicylate | about 30.0%; |
| Octylmethoxycinnamate | about 27.0%; | wherein said percentages represent the ratio of the weight of each constituent to total weight of said sunscreen composition.

22. A method of delivering a suncare product containing dihydroxyacetone for producing a uniform skin color, comprising the steps of:

a) selecting a substrate;

b) determining the dry weight of the substrate;

c) selecting a suncare product having a known percentage weight of dihydroxyacetone in solution;

d) adjusting the weight of said substrate in order to produce an application rate for achieving a desired skin color on a predetermined area of skin; and e) wetting said substrate with said suncare product.

23. The method of delivering a suncare product containing dihydroxyacetone according to claim 22, wherein the step of selecting a substrate further comprises selecting a porous substrate.

24. The method of delivering a suncare product containing dihydroxyacetone according to claim 22, wherein the step of selecting a substrate further comprises selecting a fibrous substrate.

25. The method of delivering a suncare product containing dihydroxyacetone according to claim 22, wherein the step of selecting a substrate further comprises selecting the substrate from the group consisting of cotton pads, nylon pads, rayon fiber cloth, fibrous polypropylene fabric, wet process polyester-cellulose combination fabrics and caustic entangled cotton fabric.

* * * * *